United States Patent [19]

Wetterlin

[11] Patent Number: 4,667,668
[45] Date of Patent: May 26, 1987

[54] DOSAGE INHALATOR

[75] Inventor: Kjell I. L. Wetterlin, S Sandby, Sweden

[73] Assignee: Aktiebolaget Draco, Sweden

[21] Appl. No.: 726,064

[22] Filed: Apr. 23, 1985

Related U.S. Application Data

[62] Division of Ser. No. 393,720, Jun. 30, 1982, Pat. No. 4,534,345.

[30] Foreign Application Priority Data

Jul. 8, 1981 [SE] Sweden .................................. 8104240

[51] Int. Cl.$^4$ ............................................ A61M 15/00
[52] U.S. Cl. .............................. 128/203.15; 222/636; 128/203.23
[58] Field of Search ....................... 128/203.23, 203.15; 604/57, 58; 222/345, 347, 636

[56] References Cited

U.S. PATENT DOCUMENTS 4,524,769 6/1985 Wetterlin ........................ 128/203.15

Primary Examiner—Edward M. Coven
Attorney, Agent, or Firm—Brumbaugh, Graves, Donohue & Raymond

[57] ABSTRACT

A dosage inhalator for the inhalation of a pharmacologically active compound in solution form is disclosed. The inhalator comprises a propellant container, a propellant dispensing unit, and a dosing unit for dosing the pharmacologically active compound. The dosing unit comprises a storage chamber for the active compound, a dose loading unit directly connected thereto, and a nozzle. The does loading unit comprises a movable perforated membrane, and a holder for the perforated membrane. The membrane is displaceable between a first position where a solution of active compound is introduced into the perforations of the membrane, and second position where the perforations of the membrane are inserted into a propellant passage. While the membrane is in the second position, the propellant dispensing unit may be operated, allowing propellant originally stored in the propellant container to remove the solution of the active compound from the perforations inserted into the propellant passage and carry said solution out the nozzle.

10 Claims, 8 Drawing Figures

DOSAGE INHALATOR

This aplication is a division of application Ser. No. 393,720 filed on June 30, 1982, now U.S. Pat. No. 4,534,345.

FIELD OF THE INVENTION

The present invention relates to a new dosage inhalator intended to be used at inhalation of pharmacologically active compounds. The invention also relates to a new dosage unit for measuring dosages of the active compound in solid, micronized form or in solution.

BACKGROUND OF THE INVENTION

Special requirements are made with regard to dosage inhalators intended for local administration of drugs to the respiratory tract and to the lungs. Since mostly very potent drugs are to be administered, the dose accuracy must be great. The dosage of active compound that is to be administered may be as small as 0.1 mg. It is also necessary that the particles that leave the dosage inhalator have a suitable size distribution, since too big particles tend to be deposited in the mouth.

Several systems are available for local administration of drugs to the respiratory tract and to the lungs. Among these systems may be mentioned nebulizing devices, powder inhalators which are activated by the air flow generated at inhalation, pressurized aerosols and pump inhalators.

The available systems work but are not without disadvantages.

The nebulizing devices, which are driven by a compressor, by compressed gases or by ultrasound, are relatively big and bulky and are mainly intended for stationary use. They are complicated to use. The drug administration must continue during a fairly long period of time, 5 to 10 minutes.

The use of powder inhalators has been increasing during the last few years. They are activated by the air flow generated at inhalation. When the patient inhales through the inhalator the active compound in solid, micronized form, usually kept in a capsule, is mixed with the inhaled air and administered to the respiratory tract and to the lungs of the patient. These inhalators require, of technical reasons connected with the dispensing of the active compound, a fairly great amount of active compound, 20 mg or more, in order to give an acceptable dosage accuracy. They are, therefore, only useful for low-active compounds, or for high-active compounds in combination with diluting agents, usually lactose. They are cumbersome to load and to clean, and as a rule several inhalations are necessary in order to empty a capsule. Furthermore, they are difficult to handle for certain categories of patients, and the diluting agent, lactose, is irritating at inhalation and may cause increased frequence of caries.

The pressurized aerosols are today most widely used at ambulatory treatment. Normally, they comprise a pressure unit that contains the propellant, most often different types of halogenated hydrocarbons, e.g. Freon ®, together with the active compound which either is dissolved in the propellant or suspended in the propellant in solid, micronized form. Dosage aerosols where a unit dosage of the active compound is kept separated from the propellant have also been described. Usually surface active compounds and lubricating agents are added in order to obtain a suspension which can be stored and in order to make the dosage mechanism work. The propellants, most widely used, may, furthermore, have undesirable toxicological and environmental effects.

The so called pump inhalators, finally, make use of compressed air as propellant. The active compound is normally in the form of a solution. The compression of the air is obtained by a piston system, but it is difficult in a simple manner to generate a pressure which is sufficiently high to permit an adequate particle size distribution. Furthermore, it is difficult to obtain an exact measuring of dosages of the active compound.

DESCRIPTION OF THE INVENTION

In one aspect, the present invention provides a new dosage inhalator intended for inhalation of pharmacologically active compound in solid, micronized form or in solution, said dosage inhalator comprising (a) a propellant container and a propellant dispensing unit; and (b) a dosing unit for dosing the pharmacologically active compound, characterized in that the dosing unit for dosing the pharmacologically active compound comprises a storage chamber for the active compound directly connected to a dosing unit, said dosing unit comprising a perforated membrane, a holder for the said perforated membrane, and means for displacing the membrane, whereby the membrane is displaceably arranged between a first position where active compound is introduced into the perforations in part of the area of the membrane and a second position where the said part of membrane is inserted in the propellant passage.

This dosage inhalator has the following advantages;
1. No lubricating agents need to be used.
2. Active compound in an amount from 0.1 mg, in solid micronized form or in solution, can be dispensed with sufficient accuracy and without need for use of diluting agents for active compound in solid micronized form.
3. The quality of the generated aerosol is independent of the breathing capacity of the patient.
4. Propellants under high pressure, for example liquid carbon dioxide, can be used. Thereby a particle size distribution at administration of active compound in solution can be obtained which is better than the particle size distribution which is obtained with a pump inhalator.
5. An atoxic propellant can be used, for example carbon dioxide in liquid form or in solution.

In a further aspect, the invention relates to a new dosing unit for dosing in a dosage inhalator of pharmacologically active compound in solid micronized form or in solution. The said dosing unit is characterized in that it comprises a storage chamber for the active compound in connection with a dosing unit which comprises a perforated membrane, a holder for said perforated membrane, and means for displacing the said membrane, whereby the dosing unit and the perforated membrane are displaceably arranged in relation to each other between a first position where active compound is introduced into the perforations in part of the area of the membrane and a second position where the said part area of membrane is introduced in the propellant passage of the dosage inhalator.

The dosing unit will admit dispensing active compound in solid, micronized form or in solution with sufficient dosage accuracy in an amount of from 0.1 to 5 mg. Also dosages in an amount of from 5 to 50 mg can be dispensed, especially when the active compound is in solid micronized form. The dosing unit according to the invention can be used in dosage aerosols which are activated with propellant under pressure, as well as in inhalators intended to be activated by the air flow generated at inhalation.

In a further aspect, the invention relates to the use of a perforated membrane as dosing unit for active compound in solid, micronized form in dosage aerosols.

In the preferred embodiment of the dosage inhalator and the dosing unit of the invention, the active compound is used in solid, micronized form.

Specific embodiments of the invention will now be described in detail with reference to FIGS. 1, 2, 3, 4, 5, 6, 7 and 8.

Figure 1:
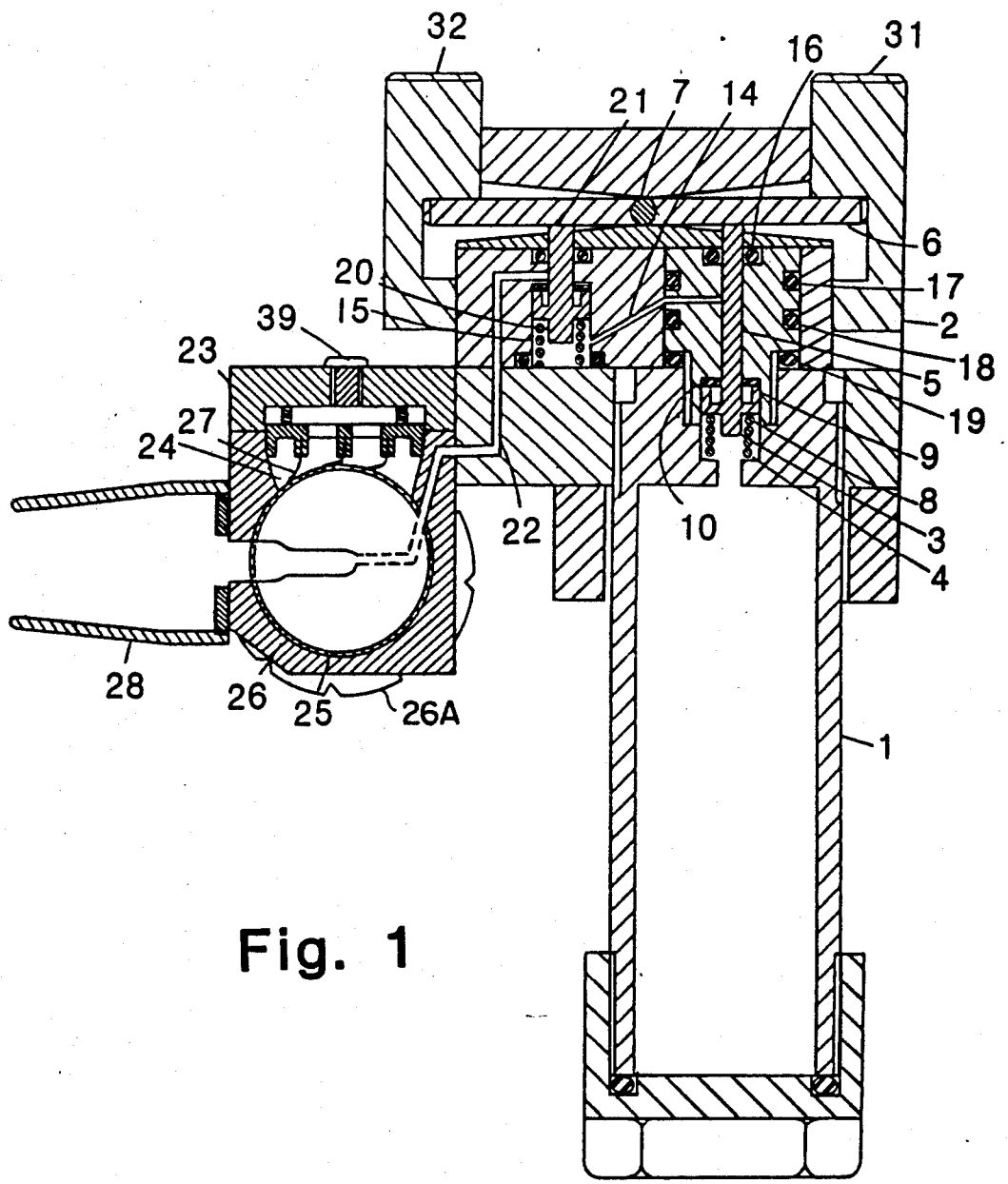
FIG. 1 is a section through a dosage inhalator for solid, micronized active compound, activated with propellant under pressure.
Figure 2:
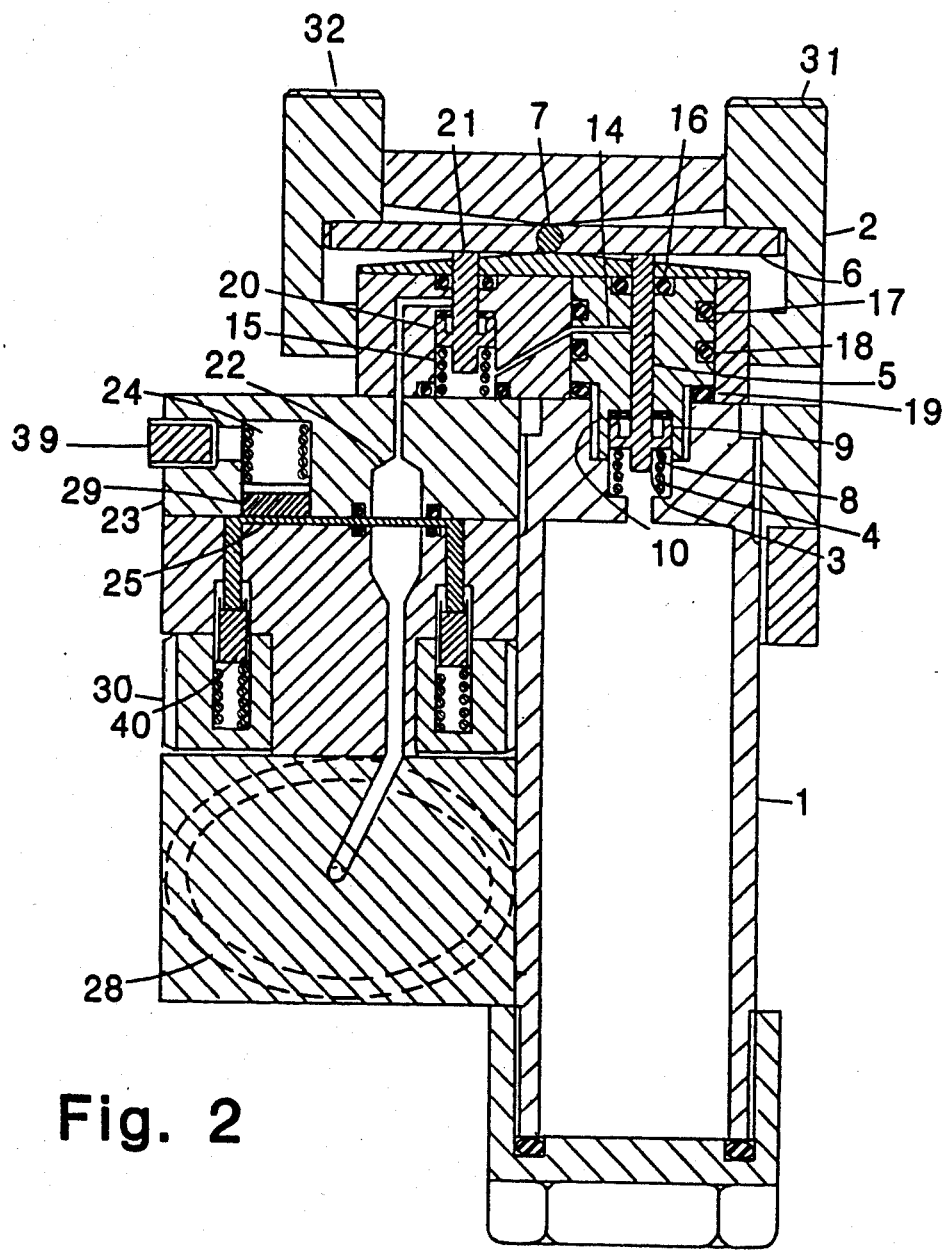
FIG. 2 is a section through a variant of the dosage inhalator of FIG. 1 for administering the active compound in solid, micronized form.

A. Dosage Inhalator for Solid, Micronized Active Compound (FIG. 1 and FIG. 2)

The dosage inhalator comprises three main components:
(a) a dosing unit 23 for dosing the pharmacologically active compound.
(b) a propellant container 1 intended for liquid and gaseous propellant.
(c) a propellant dispensing unit 2 intended for dispensing the propellant.

The propellant container 1 is manufactured in a material, for example steel, which makes it possible to use the propellant container for liquid propellants, for example halogenated hydrocarbons, and liquid carbon diozide, and for gaseous propellants. Its construction will admit use of carbon dioxide as propellant, in liquid form and in gaseous form, in spite of the high pressure, 49.5 bar at 15° C., which is required to keep carbon dioxide in liquid form. The propellant container 1 is arranged to be connected to the propellant dispensing unit 2, by a threading.

The propellant container unit comprises a first valve 3 which is arranged in the discharge passage from the propellant container 1. The valve 3 is so arranged that it automatically closes the discharge passage from the propellant container 1 when the said container is removed from the propellant dispensing unit 2. The valve 3 which is loaded with a spring 4, comprises a displaceable connecting arm 5 which co-operates with a tilting lever 6. The said tilting lever is movable around an axis 7. The valve part of the connecting arm 5 is provided with a protrusion 8 which co-operates with a depression 9 in the propellant unit 1. In the depression 9 a sealing ring 10 with rectangular section is arranged, see FIG. 5. A connecting passage 14 for propellant is arranged from the passage in which the connecting arm 5 is arranged to the dosing chamber 15 in the dosing unit 2. O-rings 16, 17, 18 and 19 seal where the connecting arm 5 attaches to the tilting lever 6 and where the connecting passage 14 reaches the propellant dispensing unit.

The passage 14 leads to a dosing chamber 15. The dosing chamber 15 comprises a spring loaded valve 20, constructed in the same manner as the valve 3 in the propellant container 1. The valve 20 comprises a movable connecting arm 21 which co-operates with the tilting lever 6.

From the dosing chamber 15 a passage 22 leads to the dosing unit 23. The dosing unit 23, which in FIG. 1 is illustrated for dispensation of solid, micronized compound, comprises a storage chamber 24 for the active compound directly connected with a dosing unit comprising a perforated membrane 25 in the form of a drum, a holder 26 for the membrane, and means for displacing the membrane, whereby the membrane is displaceably arranged between a first position where active compound in solid, micronized form is introduced into the perforations in part of the area of the membrane, and a second position where the said part of the membrane area containing a defined amount of active compound is introduced in the propellant passage 22. Active compound is brought from the storage chamber 24 into the perforations in the membrane using elastic spring-loaded scrapers 27.

In one preferred embodiment, the perforated membrane in the dosing unit 23 can be designed, as in FIG. 1, as a drum-formed rotating membrane, where the active compound is pressed into the preforations using spring-loaded scrapers 27 when the drum is brought to rotate. In another preferred embodiment, the membrane 25, see FIG. 2, is designed as a rotating disc connected to the storage chamber 24. The active compound is in this embodiment pressed into the perforations in the membrane using a spring-loaded plate 29. The perforated membrane 25 is rotated using turning means 30 so that part of the membrane area with its perforations loaded with active compound is introduced into the propellant passage 22. The turning means 30 in FIG. 2 comprise spring-loaded pins 40 which engage in dents in the perforated membrane 25 as is shown in FIG. 7.

In use the dosage inhalator according to FIG. 1 and FIG. 2 will operate as follows. The valve 3 in the propellant container 1 is opened by depressing the portion of the tilting lever 6 which is situated in connection with the valve 3, using a trigger 31. When the valve 3 is open the propellant, which can be in liquid or gaseous form, passes from the propellant unit 1 along the sides of the connecting arm 5 and via the passage 14 to the dosing chamber 15. The dosing chamber 15 is filled with propellant. When the pressure on the tilting lever above the valve 3 ceases, the valve 3 is closed by action of the combined pressure from the propellant in the propellant container 1 and the spring 4 in the valve 3. Now the valve 20 is opened by depressing, using the trigger 32, that part of the tilting lever 6 which is situated in connection with the valve 20, whereupon the propellant in the dosing chamber 15 and the propellant in the passage 14 passes along the sides of the connecting arm to the valve 20 and via the passage 22 to the dosing unit 23. The propellant will here pass that part area of the perforated membrane 25 in FIG. 1 respectively FIG. 2 which has been introduced into the propellant passage and will remove the active compound which had been loaded into the perforations in the membrane. The active compound will be driven out through the nozzle 28.

By the co-operation between the tilting lever 6 and the valves 3 and 20, the connection between the propellant container 1 and the dosing chamber 15 will be broken before the valve 20 of the dosing chamber 15 can be acted upon and the metered amount of propellant discharged. Thus, the construction of the tilting lever will admit only one of the valves 3 and 20 in the propellant container and in the dosing chamber, respectively, to be open at a given time. Both valves cannot be open simultaneously. The construction of the valve 3 in the propellant container is such that it will always be closed when the propellant container is released from the propellant dispensing unit.

Figure 6:
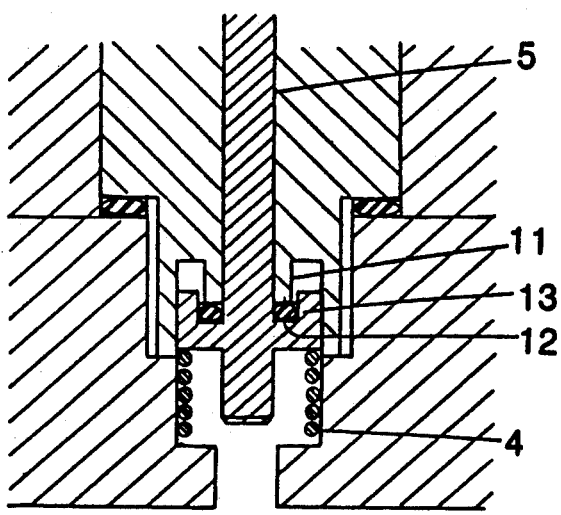
Figure 7:
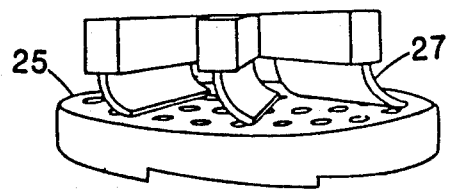
FIG. 7 shows scrapers in the storage chamber, which scrapers are used to introduce solid, micronized active compound into the perforations in a horizontal perforated membrane.

In an alternative embodiment of the valves 3 and 20, see FIG. 6, the propellant unit can be provided with a protrusion 11 which co-operates with an opposite depression 12 in the valve part of the connecting arm 5. In the depression 12 a sealing ring 13 with rectangular section is arranged.

Figure 5:
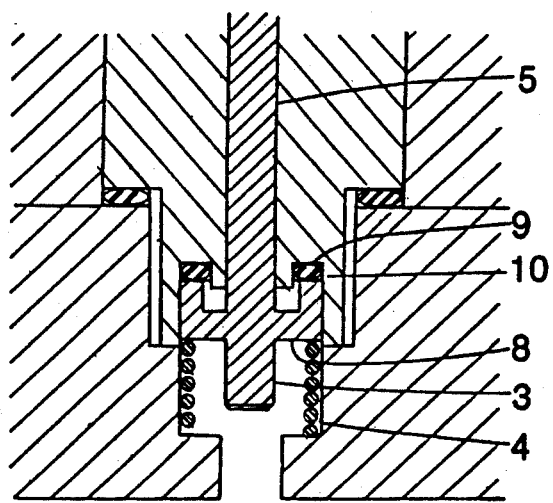
FIG. 5 and FIG. 6 illustrate embodiments of the valve in the dosing unit for propellants which is part of the dosage inhalators according to FIG. 1, FIG. 2 and FIG. 3.

The valve construction utilized in the valves 3 and 20, see FIGS. 5 and 6, is an important part of the dosage inhalator, because this valve construction makes it possible to use propellant under high pressure, for example liquid carbon dioxide, without risk for leaking.

B. Dosage Inhalator for Active Substance in Solution (FIG. 3 and FIG. 4)

Figure 3:
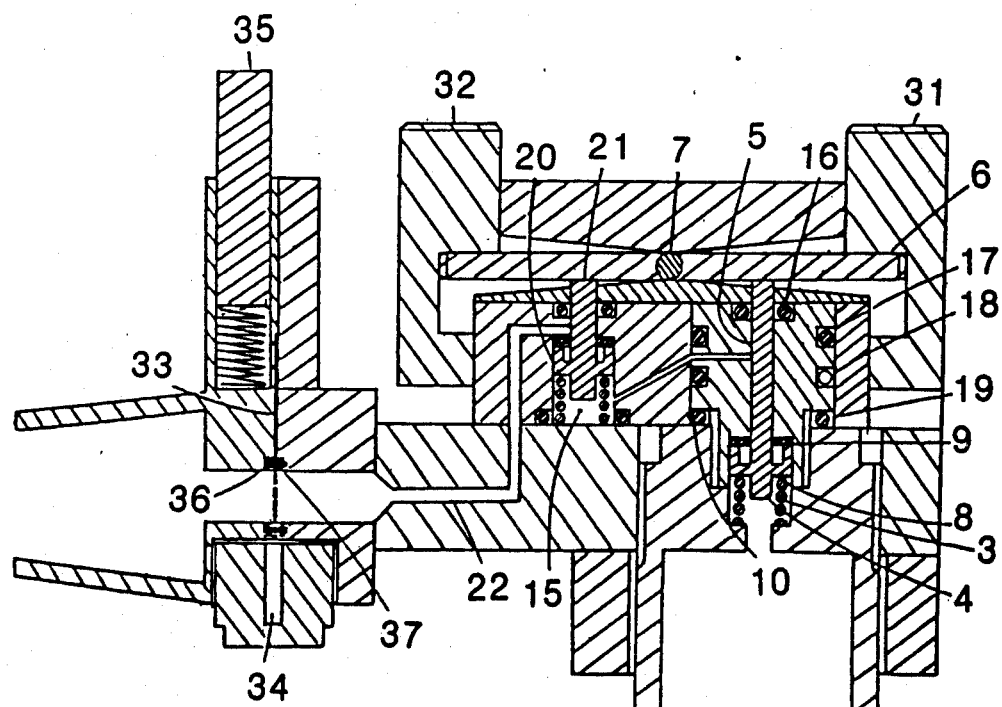
FIG. 3 is a section through a dosage inhalator for administration of active compound in solution, activated with propellant under pressure.

The dosage inhalator according to FIG. 3 differs from the dosage inhalator according to FIG. 1 only with respect to the dosing unit for the active compound, which in FIG. 3 is designed for dispensing active compound in solution. The dosing unit is arranged with a perforated membrane 33 which is arranged to be able to be displaced from a first position, where the membrane is immersed in the storage chamber 34 for active compound in solution, to a second position where the membrane is placed in the propellant passage 22. The membrane is operated with a spring-loaded trigger 35. O-rings 36 and 37 seal the connections between the membrane 33 and the propellant passage 22.

Figure 4:
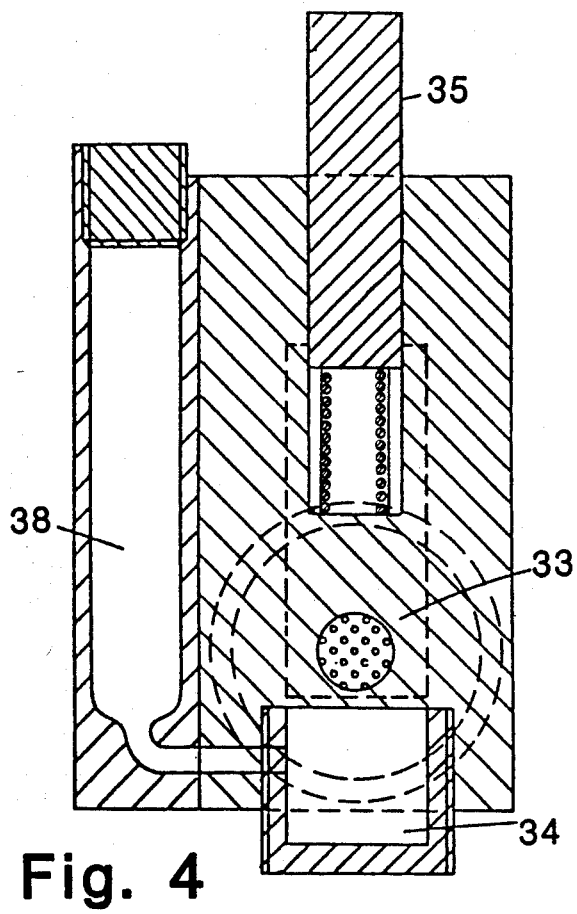
FIG. 4 is a section through a variant of the dosage unit intended for dosing active compound in solution.

FIG. 4 illustrates an alternative embodiment of the dosing unit for active compound in solution. The storage chamber 34 for active compound in solution is here connected with a second storage chamber 38 where a greater volume of the solution of the active compound can be kept. The membrane 33 can in the same way as in FIG. 3 using the trigger 35 be brought into the storage chamber 34 and then be brought into the propellant passage 22.

The size of the dosing chamber 15 may vary. Its size will depend upon whether liquid or gaseous propellant is to be dispensed. A suitable size for liquid propellant, for example liquid carbon dioxide, may be 25–300 $\mu$l. For gaseous propellants, for example gaseous carbon dioxide, a suitable size may be 50–1000 $\mu$l.

The perforated membrane can be manufactured in any suitable material, for example metal or plastic. The size of the dosage of active compound which is to be administered is determined by the size of the perforations in the membrane, the thickness of the membrane, and the number of perforations that is brought into the propellant passage, and by the area of the propellant passage. The accuracy of the dosage will mainly depend on the accuracy in the manufacturing of the membrane. Examples of perforated membranes that can be used are the metal nets which are manufactured by Veco Beheer B. V., Eerbeek, The Netherlands. These nets can be obtained with various sizes of the perforations. They can be formed in desired manner, for example in drum form or they can be used in the form of horizontal, plane membranes. Also woven nets of metal, fiber or of other materials can be used, especially at administration of active compound in solution. The important factor is the dosage accuracy that can be obtained.

Figure 8:
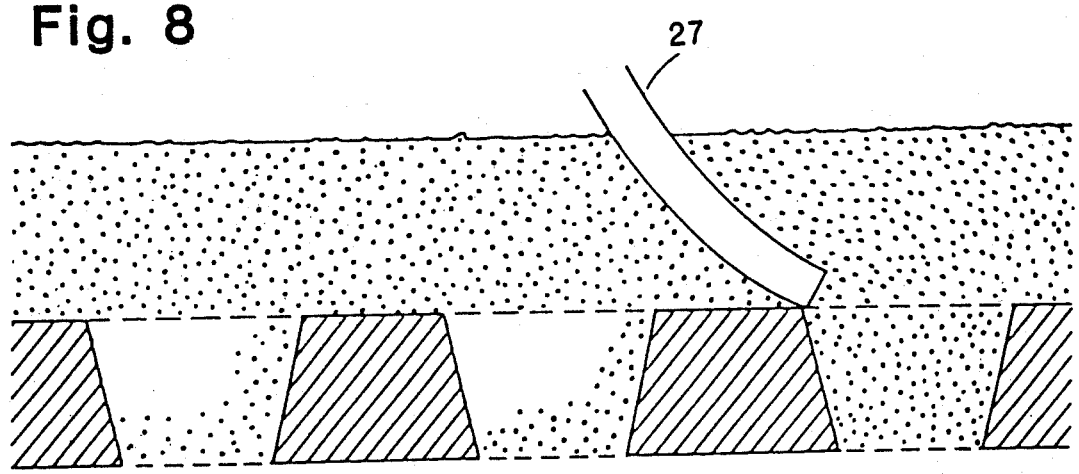
FIG. 8 shows how solid, micronized active compound is fed from the storage unit into the perforations in the perforated membrane using the said scrapers.

At dispensing of active compound in solid, micronized form, it is preferred that the perforations in the perforated membrane are in the form of truncated cones with their larger area directed towards the nozzle. Such a construction will partly facilitate the loading of the membrane with active compound, partly facilitate the emptying of the perforations when the active compound is administered. See FIG. 8.

The perforated membrane, when it is in the form of a drum, can be arranged for loading from the outside as well as from the inside of the drum.

The perforations in the perforated membranes can be of arbitrary design. They can be circular, square, elliptic, rectangular or have other geometrical form. The area of the perforations in the membrane can be a large or a small part of the membrane area, for example from 1 to 95%, whereby the term "membrane area" refers to that area of the membrane which is inserted into the propellant passage. The number of perforations in the membrane area can vary depending on factors such as the amount of active compound that is to be administered per dosage, the physical properties of the active compound, etc. In a preferred embodiment, the perforations have conical shape, as said above, at dosing of solid, micronized compound.

At administration of active compound in solution the construction of the perforated membrane including the form of the perforations is less critical. Also membranes in the form of nets, for example woven nets in metal or in fiber can be used, as mentioned above.

The size of the dosages of bronchospasmolytically active compounds, or steroids for inhalation, that normally are administered at each administration is as follows.

Terbutaline: standard dosage 0.5 mg
Salbutamol: standard dosage 0.2 mg
Budesonide: standard dosage 0.1 mg The active compound can be administered in micronized form without additional ingredients or in pharmaceutically modified micronized form in order to obtain improved flow properties. The micronized particles may be covered with a film functioning for example by masking bitter taste of the active compound, or by providing slow release of the active compound in the respiratory tract.

The dosing unit in the dosage inhalator according to the present invention admits dispensing of an amount of active compound of mainly from 0.1 to 1 mg, but also dosages from 1 to 5 mg and from 5 to 50 mg, especially when solid, micronized active compound is used, can be dispensed by suitable design of perforations and size of that part of the area of the perforated membrane which is intended to be introduced into the propellant passage.

The storage chamber 24 for active compound in solid, micronized form, respectively the storage chamber 34 for active compound in solution can be intended to contain active compound for about 100 to 200 dosages, which is sufficient for about a month's normal use for local administration of active compound to the respiratory tract.

The storage chamber 24 for solid, micronized compound can be placed above as well as below the perforated membrane. In a preferred embodiment the storage chamber is placed above the membrane. The storage chamber 24 can be arranged to be refilled via a sealable opening 39.

The storage chamber 34 for active compound in solution is in one preferred embodiment connected with a larger sealable storage chamber 38.

In a preferred embodiment of the dosage inhalator according to the invention the perforated membrane 25 is displaceably arranged in relation to the storage chamber 24.

What we claim is:

1. An inhaler for administering a solution of a phramacologically active compound to a patient as droplets suspended in a propellant comprising:
    a gas conduit through which a dose of said solution suspended in said propellant is supplied to said patient, a storage chamber means for storing said solution, a perforated membrane having a plurality of preselected portions each adapted to hold and dispense a reproducible unit dose 'less than 50 mg of said compound in solution, and a propellant supply unit for supplying a pharmacologically acceptable propellant to the inhaler,
    said conduit, membrane and propellant supply unit being operably connected to each other so that propellant released from the propellant supply unit passes through one of said preselected portions of said perforated membrane that is positioned across said gas conduit, releases said solution carried thereby, and carries said solution as suspended droplets through said gas conduit to the patient,
    wherein said perforated membrane is adapted to be displaceable through a plurality of positions in each of which another preselected portion thereof holding a reproducible dose of said solution is moved into a dispensing postion relative to said gas conduit and propellant supply unit, and another portion thereof is moved into said storage chamber, and
    whereby reproducible doses of the solution can be transferred from said storage chamber means by said membrane, positioned across said gas conduit by said membrane, and removed therefrom by propellant discharged from said propellant supply unit.

2. An inhaler according to claim 1 wherein the perforated membrane is displaceably arranged for rotation relative to the storage chamber.

3. An inhaler according to claim 1 wherein said perforated membrane is a rotatable drum.

4. An inhaler according to claim 1 including a dosing chamber, first passage means connecting said propellant supply unit to said dosing chamber for passage of propellant therebetween, and second passage means connecting said dosing chamber to said perforated membrane for passage of propellant therebetween, first valve means in said first passage for controlling the flow of propellant therethrough, and second valve means in said second passage means for controlling the passage of propellant therethrough,
    said first and second valve being arranged so that only one valve may be opened at any one time, said first valve when opened allowing propellant stored in said propellant supply unit to flow into said dosing chamber and when closed prohibiting said flow, and said second valve when opened allowing propellant stored in said dosing chamber to flow into said propellant passage and when closed prohibiting said flow into said passage,
    whereby the amount of propellant discharged for each dose is controlled by the amount of propellant stored in said dosing chamber.

5. An inhaler according to claim 4 including a tilting lever adapted to interconnect said first valve and said second valve such that only one of said valves may be opened at any one time.

6. An inhaler according to claim 5 wherein each of said valves includes a spring biasing the valve to its normally closed position.

7. An inhaler according to claim 1 wherein each preselected portion has a plurality of perforations of substantially the same size, each such perforation being adapted to hold and dispense a share of the dose dispensed by said preselected portion.

8. A dosing unit adapted for use in an inhaler for administering to a patient a unit dose of a solution of a pharmacologically active compound suspended in the form of droplets in a propellant through a gas conduit, said propellant being supplied from a propellant supply unit to said gas conduit through propellant conduit means, comprising:
    a storage chamber means for storing said solution;
    a perforated membrane adapted to hold and dispense said solution in a plurality of preselected portions adapted to hold a reproducible volume of said solution, including at least a first and second portion;
    holding means for holding said first portion of said membrane in a loading position in said storage chamber means and adapted to hold said second portion of said membrane in a dispensing position between said gas conduit and said propellant conduit means; and
    means for displacing said membrane on said holding means so that said first portion of said membrane can be moved into said dispensing position as said second portion can be moved into said loading position,
    whereby a controlled amount of the solution can be loaded from said storage chamber means into one of said preselected portions and transported by said displacing means to a position from where it is adapted to be removed by propellant flowing through said propellant conduit means and said gas conduit passage thereby to the patient.

9. A dosing unit according to claim 8 wherein the perforated membrane is displaceably arranged for rotation relative to the storage chamber.

10. A dosing unit according to claim 8 wherein said perforated membrane is a rotatable drum.

* * * * *